United States Patent
Salib et al.

[11] Patent Number: 5,258,031
[45] Date of Patent: Nov. 2, 1993

[54] INTERVERTEBRAL DISK ARTHROPLASTY

[75] Inventors: Richard M. Salib, Excelsior, Minn.; Kenneth A. Pettine, Fort Collins, Colo.

[73] Assignee: Danek Medical, Memphis, Tenn.

[21] Appl. No.: 990,925

[22] Filed: Dec. 14, 1992

Related U.S. Application Data

[63] Continuation of Ser. No. 817,052, Jan. 6, 1992, abandoned.

[51] Int. Cl.⁵ .................................................. A61F 2/44
[52] U.S. Cl. .......................................... 623/17; 606/61
[58] Field of Search ................ 623/16, 18, 17; 606/61

[56] References Cited

U.S. PATENT DOCUMENTS

| | | | |
|---|---|---|---|
| Re. 32,449 | 6/1987 | Claussen et al. | 623/22 X |
| 4,349,921 | 9/1982 | Kuntz | 623/17 |
| 4,595,663 | 6/1986 | Krohn et al. | 623/66 X |
| 4,714,469 | 12/1987 | Kenna | 623/17 |
| 4,759,769 | 7/1988 | Hedman et al. | 623/17 |
| 4,863,476 | 9/1989 | Shepperd | |
| 4,932,975 | 6/1990 | Main et al. | |
| 4,936,848 | 6/1990 | Bagby et al. | |
| 4,946,378 | 8/1990 | Hirayama et al. | 623/17 |
| 4,997,432 | 3/1991 | Keller | 623/17 X |
| 5,002,576 | 3/1991 | Fuhrmann et al. | 623/17 |
| 5,037,438 | 8/1991 | Davidson | 623/18 |

FOREIGN PATENT DOCUMENTS

WO92/14423  9/1992  PCT Int'l Appl.

*Primary Examiner*—David Isabella
*Assistant Examiner*—Dinh X. Nguyen
*Attorney, Agent, or Firm*—Woodard, Emhardt, Naughton, Moriarty & McNett

[57] ABSTRACT

A prosthetic disk having ball and socket members made of a material having expected durability to function properly for 40 years in a typical lumbar spine. The disk is shaped to provide movement in 6 degrees of freedom mimicking normal intervertebral movement, except compression. The arthroplasty device is non-compressible to maintain distraction of the facet joints posteriorly. Base plates with tabs can be fastened to the ball and socket members to ensure short-term and long-term fixation, although it is expected not to be necessary.

13 Claims, 2 Drawing Sheets

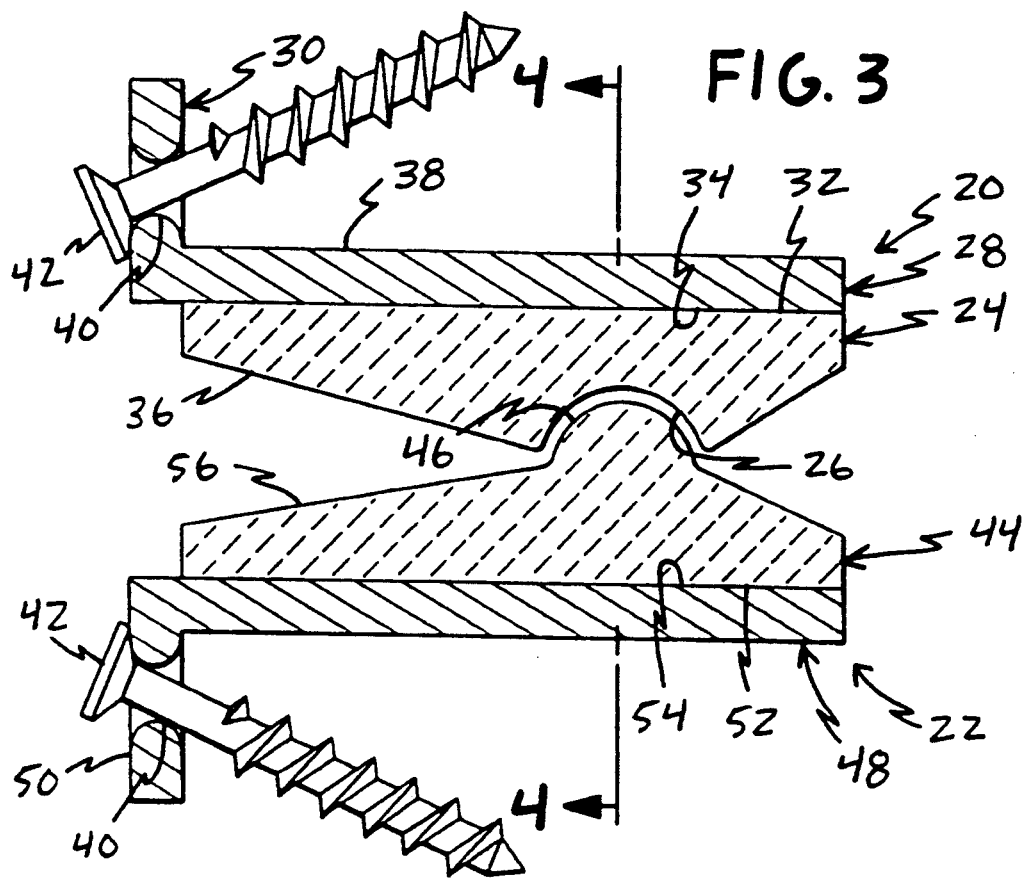
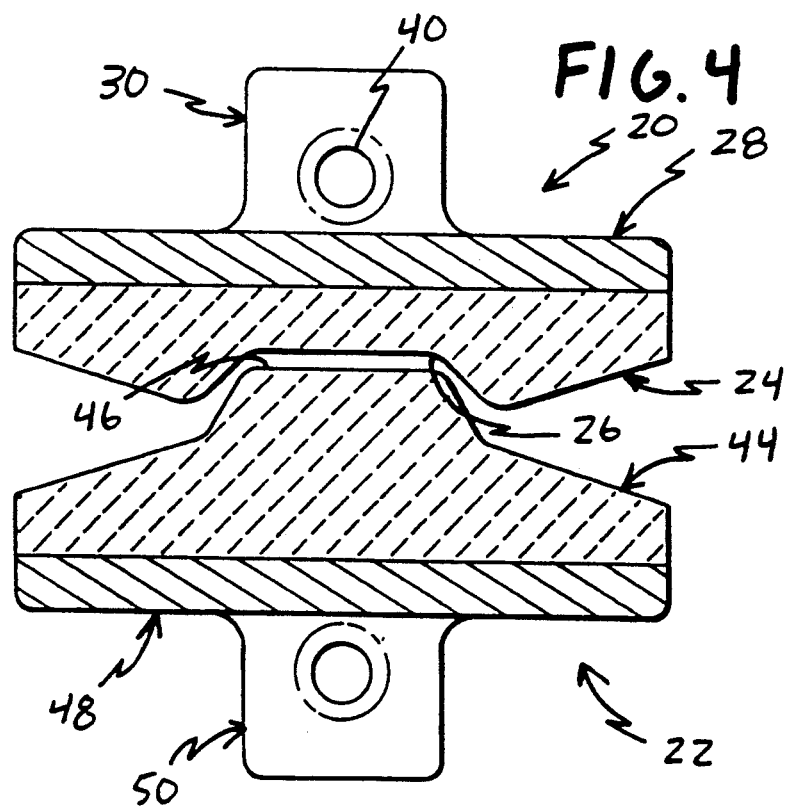

INTERVERTEBRAL DISK ARTHROPLASTY

This application is a continuation of application Ser. No. 07/817,052, filed Jan. 6, 1992, now abandoned.

FIELD OF THE INVENTION

The present invention is directed to a surgical joint replacement device; particularly, a replacement for a ruptured disk between consecutive vertebrae in the spine.

BACKGROUND OF THE INVENTION

Currently there are approximately 60,000 lumbar spine fusions performed in the United States and 30,000 lumbar fusions performed in Canada each year. Spinal fusion is frequently used as a treatment for low back pain and intervertebral disk degeneration, and the use of internal fixation has increased the ability of a surgeon to obtain a solid fusion. There is increased concern, however, that the biomechanical rigidity of internal fixation may predispose adjacent spinal motion segments to rapid deterioration. Long-term follow up of patients undergoing a successful fusion indicates that 50 percent will continue to have complaints of pain. As in other joints, alternatives to fusing a spinal motion segment have inherent advantages.

Researchers have attempted to design a successful intervertebral disk arthroplasty for years. U.S. Pat. No. 4,946,378 discloses an artificial disk having a pair of end bodies with a medical synthetic polymeric intermediate member held between the end bodies. The intermediate member apparently provides some flexibility. Somewhat similarly, U.S. Pat. No. 5,002,576 discloses an artificial disk having end cover plates separated by a closed corrugated tube which is filled with a visco elastic material, like a body-compatible silicone.

Other approaches are shown in U.S. Pat. Nos. 4,759,769 and 4,997,432. U.S. Pat. No. 4,759,769 discloses an artificial disk having upper and lower members hinged together at a rear portion and biased apart at a front portion by stiff coil springs. U.S. Pat. No. 4,997,432 shows an artificial disk having plates separated by a sliding core body normally consisting of a synthetic material.

Although prosthetic disks continue in development, none is yet recognized as solving the disk replacement problem. There are certain basic criteria a successful intervertebral disk arthroplasty must fulfill. Fatigue strength of the materials is of utmost importance. Since the average age of patients undergoing spinal fusion is 42 years old, the life span of the device should exceed 40 years. Assuming the average person experiences 2 million strides per year and 125,000 significant bends in the spine, a conservative estimate of the number of spinal loading cycles over the 40-year period would be 85 million cycles. To provide a factor of safety, the device should be designed to at least a fatigue limit of 100 million cycles.

In addition to such durability, the materials for a successful intervertebral disk arthroplasty must be biocompatible. The volume of wear must be kept to a minimum. Although the implant should be small enough to be contained within the anatomic confines of a normal disk space, it is recognized that it may be advantageous to increase the prosthetic disk height in order to over distract the disk space to unload the facet joints posteriorly. Projections from this space may be used to provide short-term fixation, but there should then also be provision for disks to be implanted at contiguous spaces with no overlap of projections.

The present invention not only satisfies these criteria, but it is anticipated that it could be a successful arthroplasty in place of 90 percent of the fusions currently being performed.

SUMMARY OF THE INVENTION

The present invention is directed to an intervertebral disk arthroplasty comprising a first member having a socket and a second member having a ball fitting in the socket. With respect to a space created by a resected disk from between first and second vertebrae, the first member fits adjacent the first vertebrae and the second member fits adjacent the second vertebrae so that the ball fits in the socket.

On the one hand, it may be advisable to fasten a first base plate having a first tab to the first member and to fasten a second base plate having a second tab to the second member in order to pass screws through the first and second tabs to fasten the base plates and first and second members to first and second vertebrae, respectively. On the other hand, initial screw fixation may not be necessary since it has been shown that bone ingrowth occurs into ceramic, the preferred material for the first and second members being zirconium oxide ceramic. Although human cadaver analysis may be necessary, as well as in vivo animal testing, clinical investigative implantation in humans will ultimately be needed to establish complete confidence in the material. Nevertheless, the anticipated results of use of the material leads to optimism that the present invention will be found to satisfy all the criteria of a successful intervertebral disk arthroplasty. The indicated ceramic is biocompatible and the fatigue strength is expected to provide the necessary number of design cycles for the indicated use. Wear would be minimal and the implant can be made small enough to fit within the anatomic confines of a normal disk space. Although zirconium oxide ceramic is presently preferred, it is understood that other materials may be found which will also satisfy performance needs.

In any case, with material criteria satisfied, the invention then further provides for movement in 6 degrees of freedom mimicking normal intervertebral disk movement, except for compression. The invention arthroplasty is designed to be non-compressible in order to maintain distraction of the facet joints posteriorly, thereby reducing the likelihood of a source of possible pain.

The arthroplasty is placed in a distracted disk space so that the surrounding soft-tissue is in tension. This prevents the arthroplasty from dislocating. In this environment, the ball and socket as defined by the invention eliminates any loose moving parts, while providing for a loose fit so that the greatest flexibility of movement is available.

Thus, the advantages and objects obtained by the present invention are many. Further explanation and understanding is available, however, by reference to the drawings briefly described hereinafter and to the detailed description thereafter.

BRIEF DESCRIPTION OF THE DRAWINGS

FIG. 3 is a side view of a disk arthroplasty device in accordance with the present invention; and FIG. 4 is a front view of the device of FIG. 3.

DETAILED DESCRIPTION OF THE PREFERRED EMBODIMENT

Figure 2:
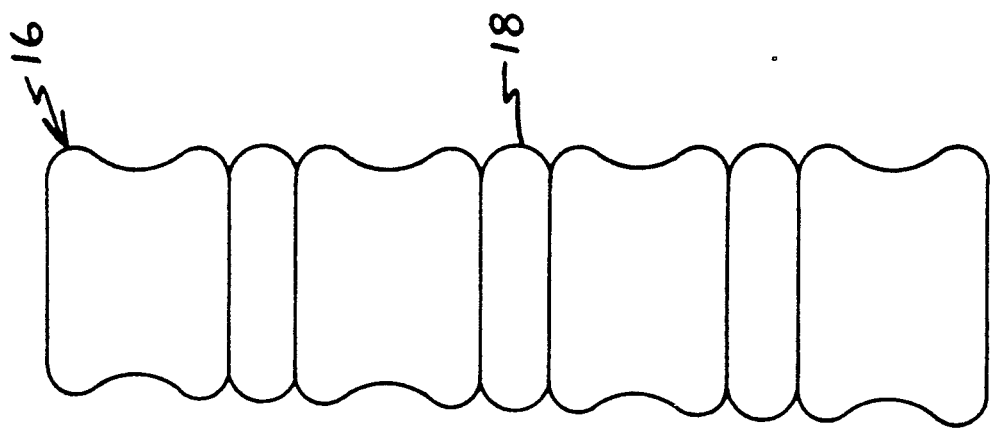
FIG. 2 is similar to FIG. 1, except a healthy disk has been replaced by a disk arthroplasty in accordance with the present invention.
Figure 1:
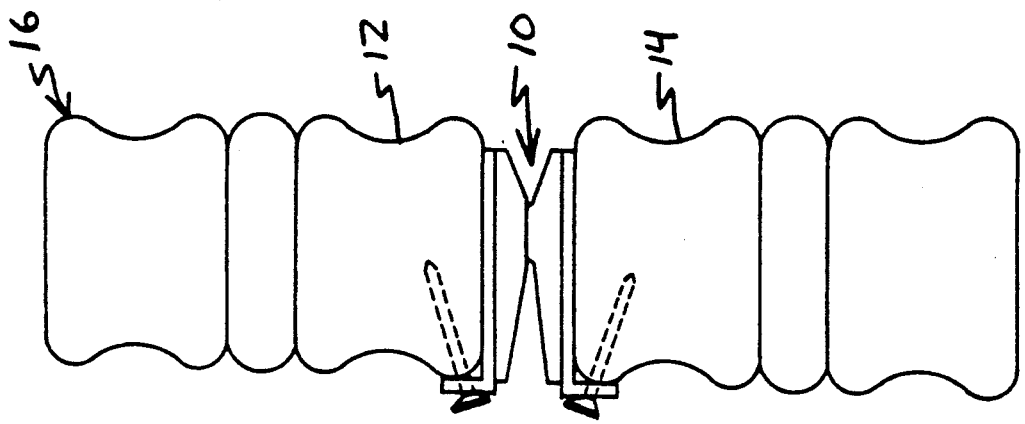
FIG. 1 is a front view of a lumbar spine showing healthy disks between vertebral bodies.

Referring now to the drawings wherein like reference numerals designate identical or corresponding parts throughout the several views, and more particularly to FIG. 2, an intervertebral disk arthroplasty device in accordance with the present invention is designated generally by the numeral 10. Device 10 is shown implanted between a first vertebral body 12 above it and a second vertebral body 14 below it, all being part of a representative lumbar spinal column 16. Lumbar spine 16 is shown in FIG. 1 to include a healthy disk 18. Device 10 is a prosthetic disk replacement in the space created by resected disk 18.

As shown in FIGS. 3 and 4, disk arthroplasty device 10 includes an upper assembly 20 and a lower assembly 22. Upper assembly 20 includes a first member 24 having a socket 26 therein. A base plate 28 having an upwardly extending tab 30 therefrom is fastened to first member 24. First member 24 has an upper side 32 to conform with and be fastened to an adjacent side 34 of base plate 28. A side 36 opposite upper side 32 includes socket 26 formed therein. Side 36 is formed so that it slopes upwardly on all sides of socket 26 such that the sloping is away from the entrance to socket 26 and toward upper side 32.

Base plate 28 is essentially a flat plate fastened with a biocompatible adhesive or other fastening mechanism known to those skilled in the art along side 34 to side 32 of first member 24. The upper side 38 of base plate 28 is formed to conform with vertebral body 12. Generally, side 38 is flat, and the conforming side 40 of vertebral body 12 is made flat during the surgery. Tab 30 extends upwardly and is integral with base plate 28. Tab 30 includes an opening 40 therethrough so that a screw 42 (shown with respect to lower base plate 48) can be used to fasten assembly 20 to vertebral body 12.

Lower assembly 22 includes a second member 44 having a ball 46 formed thereon which fits loosely into socket 26. Base plate 48 having tab 50 is similar to upper base plate 28 with tab 30 and need not be described further. First member 44 has a lower side 52 which is fastened to an adjacent side 54 of base plate 48 and in a similar fashion as earlier described with respect to first member 24 and upper base plate 28. A side 56 opposite from lower side 52 includes ball 46 extending upwardly therefrom. Side 56 slopes away from ball 46 on all sides of ball 46 so as to create space between first and second members 24, 44 except where they fit together at ball 46 and socket 26. In a presently preferred embodiment, sides 56 and 36 slope away from ball 46 and socket 26 along an inclined plane in four different directions. Ball 46 and socket 26 generally have an oval shape or an elongated shape with quarter spherical shapes at the ends.

A motion segment with respect to the present invention comprises a disk arthroplasty device 10 and adjacent upper and lower vertebral bodies. The exact contours of ball 46 and socket 26 and the surrounding surfaces of sides 36 and 56 determine the range of motion allowed in flexion and extension, side bending, shear and rotation of the motion segment.

The primary motion observed in a healthy lumbar intervertebral joint is flexion-extension. A typical L4–L5 intervertebral disk allows 13 degrees of flexion, 3 degrees of extension, 3 degrees of lateral side bending, 1 degree of axial rotation, and a small amount of shear. The center of rotation for flexion-extension is located in the posterior portion of the intervertebral disk space. The present invention is based on a concept of loose constraint. The design allows 6 degrees of freedom mimicking the normal intervertebral disk except for compression. The disk arthroplasty device is designed to be non-compressible to maintain distraction of the facet joints posteriorly. In addition, it is inserted by distracting the disk space which will place the surrounding soft tissue constraints in tension. This helps prevent the arthroplasty device from dislocating. The device is shaped to provide 15 degrees of flexion, 5 degrees of extension, 5 degrees of side bending, 5 degrees of rotation, and 2 millimeters of shear. The articulating surfaces are the concave female socket surface which articulates with the male concave ball surface. Such design eliminates loose moving parts.

Zirconium oxide ceramic is presently preferred as the articulating material for both the convex and concave surfaces. Zirconium oxide ceramic is commercially available from Smith & Nephew Richards, 1450 Brooks Road, Memphis, Tenn. 38116. The material specifications show ideal wear characteristics and biocompatibility. The modulus of elasticity is less than previously available ceramics, and is less prone to cracking. It would appear that the material would last the required 40 years as a replacement disk arthroplasty.

The present invention as disclosed in the FIGURES has the zirconium oxide ceramic fastened to base plates made preferably from either chrome cobalt or titanium. The purpose for the metal base plates is to enhance bone ingrowth for long-term fixation and to provide for short-term fixation with screw attachments to adjacent vertebral bodies. However, it is understood that since device 10 is placed in distracted disk space wherein surrounding soft tissue constraints are in tension, that initial screw fixation may not be necessary. Furthermore, bone ingrowth has been shown to occur into ceramic. It is anticipated, therefore, that the entire disk arthroplasty device may be able to be made of only first and second members 24, 44, namely the two articulating pieces of ceramic.

An appropriate surgical technique for implacement of the present invention is described in a paper, herein incorporated by reference, entitled "Femoral Cortical Ring Plus Cancellous Dowel: An Alternative in an Interior Lumbar Interbody Fusion" available from Richard M. Salib, M.D., Institute for Low Back Care, 2800 Chicago Avenue South, Minneapolis, Minn. 55407.

Thus, characteristics and advantages of the present invention, together with details of the structure and function, have been set forth in accordance with a preferred embodiment in the disclosure. It is understood, however, that the disclosure is illustrative and that changes, especially in matters of shape, size, and arrangement, to the full extent of the general meaning in the terms in which the claims are expressed, are within the principle of the invention.

What is claimed is:

1. An intervertebral disk arthroplasty adapted to replace a disk between a first vertebra and a second vertebra in the spine, said arthroplasty comprising:
   a first member engaging the first vertebra having a first joint surface, a first posterior end and a first anterior end, said ends defining a transverse midline therebetween, said midline being equidistant from said first anterior end and said first posterior end;
   a second member for engaging the second vertebra having a second joint surface facing said first joint surface, and second posterior and anterior ends juxtaposed with corresponding ends of said first posterior and anterior ends;
   a ball and socket joint between said first and second members defined in said first and second joint surfaces and disposed between said midline and said first posterior end, said ball and socket joint configured to permit relative rotation between said first member and said second member about a first axis parallel to said transverse midline and a second axis perpendicular to said first axis and lying in a plane.

2. The intervertebral disk arthroplasty of claim 1 wherein said first and second joint surfaces are inclined away from said ball and socket joint toward said first and second surfaces, respectively, entirely around said joint.

3. The intervertebral disk arthroplasty of claim 2, wherein each of said first and second joint surfaces includes a first inclined face extending from said transverse midline to said posterior end at a first angle relative to said respective joint surface, and a second inclined face extending from said transverse midline to said anterior end at a second angle relative to said respective joint surface, said second angle being greater than said first angle.

4. The intervertebral disk arthroplasty of claim 1, wherein said ball and socket joints includes a ball portion defined on said first joint surface of said first member that is elongated along said first axis and a socket portion correspondingly defined in said second joint surface of said second member to receive said ball portion therein.

5. The intervertebral disk arthroplasty of claim 4, wherein:
   said first and second axes are in a plane parallel to said plane and
   said elongated ball portion has opposite ends along said first axis and is received within said socket portion with a first predetermined spacing between said ball portion and said opposite ends to permit relative rotation up to about 5° between said first and second members about said second axis.

6. The intervertebral disk arthroplasty of claim 5, wherein said elongated ball portion is partially cylindrical in cross-section along said first joint surface and includes opposite ends formed in a partial spherical shape.

7. The intervertebral disk arthroplasty of claim 5, wherein said elongated ball portion is received within said socket portion with a second predetermined loose fit along said second joint surface to permit relative rotation up to about 5° between said first and second members about a third axis perpendicular to said first and second axes.

8. The intervertebral disk arthroplasty of claim 1 further comprising:
   a first base plate fastened to said first member opposite said first joint surface; and
   a second base plate fastened to said second member opposite said second joint surface;
   each of said base plates having a surface for engaging a respective vertebra of the first and second vertebrae.

9. The intervertebral disk arthroplasty of claim 8 wherein:
   said first base plate includes a first tab extending generally perpendicularly therefrom; and
   said second base plate includes a second tab extending generally perpendicularly therefrom,
   each of said first and second tabs having a surface for engaging the first and second vertebra, respectively, and openings for receiving screws for fastening to the first and second vertebrae, respectively.

10. The intervertebral disk arthroplasty of claim 9, wherein said openings of each of said first and second tabs include a curved surface to permit angulation of the screw relative to said tabs.

11. The intervertebral disk arthroplasty of claim 1 wherein said first and second members are formed of a zirconium oxide ceramic.

12. An intervertebral disk arthroplasty for a space created by a disk resected from between a first vertebra and a second vertebra, comprising:
   a first member having a first side adapted to be placed adjacent the first vertebra, said first member also having a side opposite said first side which includes an elongated socket formed therein, said side opposite said first side all around said socket being inclined away from said socket toward said first side:
   a second member having a second side adapted to be placed adjacent the second vertebra, said second member also having a side opposite said second side which includes an elongated ball formed therein, said side opposite said second side all around said ball being inclined away from said ball toward said second side, said ball fitting loosely in said socket.

13. An intervertebral disk arthroplasty adapted to replace a disk between a first vertebra and a second vertebra in the spine, said arthroplasty comprising:
   a first member having a first surface for engaging the first vertebra, an opposite first joint surface, a first posterior end and a first anterior end, said ends defining a transverse midline therebetween said midline being equidistant from from said first anterior end and said posterior end;
   a second member having a second surface for engaging the second vertebra, an opposite second joint surface facing said first joint surface, and second posterior and anterior end juxtaposed with corresponding ones of said first posterior and anterior ends;
   a joint between said first and second members to permit relative rotation between said first member and said second member about a first axis parallel to said transverse midline and a second axis perpendicular to said first axis, said joint including:
      a ball portion defined in said first joint surface of said first member, said ball portion having a partially cylindrical cross-section along an axis parallel to said transverse midline terminating in opposite end faces that are sloped toward said first joint surface; and
      a socket portion defined in said second joint surface substantially complementary to said ball portion in said first joint surface and configured to loosely receive said ball portion therein.

* * * * *